United States Patent
Orszulak

(10) Patent No.: US 9,649,146 B2
(45) Date of Patent: May 16, 2017

(54) ELECTRO-THERMAL DEVICE

(71) Applicant: COVIDIEN LP, Mansfield, MA (US)

(72) Inventor: James H. Orszulak, Nederland, CO (US)

(73) Assignee: COVIDIEN LP, Mansfield, MA (US)

(*) Notice: Subject to any disclaimer, the term of this patent is extended or adjusted under 35 U.S.C. 154(b) by 678 days.

(21) Appl. No.: 13/973,543

(22) Filed: Aug. 22, 2013

(65) Prior Publication Data
US 2014/0094794 A1 Apr. 3, 2014

Related U.S. Application Data

(60) Provisional application No. 61/708,852, filed on Oct. 2, 2012.

(51) Int. Cl.
*A61B 18/12* (2006.01)
*A61B 18/08* (2006.01)
(Continued)

(52) U.S. Cl.
CPC ........ *A61B 18/1206* (2013.01); *A61B 18/08* (2013.01); *A61B 18/082* (2013.01);
(Continued)

(58) Field of Classification Search
CPC ....... A61B 18/08; A61B 18/082; A61B 18/12; A61B 18/1206; A61B 2018/00642;
(Continued)

(56) References Cited

U.S. PATENT DOCUMENTS 3,760,812 A 9/1973 Timm et al.
3,895,635 A 7/1975 Justus et al.
(Continued)

FOREIGN PATENT DOCUMENTS

CN 1233944 A 11/1999
CN 1610526 A 4/2005
(Continued)

OTHER PUBLICATIONS

Extended European Search Report corresponding to European Application No. 13186383.9 dated Feb. 27, 2014; 9 pages.
(Continued)

*Primary Examiner* — Ronald Hupczey, Jr.
*Assistant Examiner* — Khadijeh Vahdat

(57) ABSTRACT

An electro-thermal apparatus configured to treat tissue is provided. The electro-thermal apparatus including an electrosurgical cable configured to couple to an electrosurgical energy source. The electrosurgical cable includes supply and return lines that are wound in a double helix arrangement around a dielectric insulator within the electrosurgical cable. An electro-thermal element is provided at a distal end of the electrosurgical cable. The electro-thermal element is in electrical communication with the supply and return lines via corresponding first and second conductive traces. The first and second conductive traces have a patterned geometry and resistivity configured to convert electrical energy provided by the supply and return lines to thermal energy for treating tissue.

20 Claims, 3 Drawing Sheets

(51) Int. Cl.
  *A61B 17/00* (2006.01)
  *A61B 18/00* (2006.01)
(52) U.S. Cl.
  CPC ............... *A61B 2017/00057* (2013.01); *A61B 2018/0072* (2013.01); *A61B 2018/00642* (2013.01); *A61B 2018/00702* (2013.01); *A61B 2018/00714* (2013.01); *A61B 2018/00755* (2013.01); *A61B 2018/00767* (2013.01); *A61B 2018/00779* (2013.01); *A61B 2018/00791* (2013.01); *A61B 2018/00797* (2013.01); *A61B 2018/00827* (2013.01); *A61B 2018/00875* (2013.01); *A61B 2018/00892* (2013.01)
(58) Field of Classification Search
  CPC  A61B 2018/00702; A61B 2018/00714; A61B 2018/0072; A61B 2018/00755; A61B 2018/00767; A61B 2018/00779; A61B 2018/00791; A61B 2018/00797; A61B 2018/00827; A61B 2018/00875; A61B 2018/00892; A61B 2017/00057
  USPC ..................................... 606/27–52
  See application file for complete search history.

(56) References Cited

U.S. PATENT DOCUMENTS

| | | | |
|---|---|---|---|
| 4,413,304 A | 11/1983 | Gerry | |
| 5,693,045 A | 12/1997 | Eggers | |
| 5,831,210 A | 11/1998 | Nugent | |
| 6,113,596 A | 9/2000 | Hooven et al. | |
| 6,190,385 B1 | 2/2001 | Tom et al. | |
| 6,300,573 B1 | 10/2001 | Horie | |
| 6,322,559 B1* | 11/2001 | Daulton | A61B 18/1492 606/41 |
| 6,379,349 B1 | 4/2002 | Muller et al. | |
| 6,394,949 B1 | 5/2002 | Crowley et al. | |
| 7,057,111 B2 | 6/2006 | Fung et al. | |
| 7,090,673 B2 | 8/2006 | Dycus et al. | |
| 7,147,638 B2 | 12/2006 | Chapman et al. | |
| 7,156,846 B2 | 1/2007 | Dycus et al. | |
| 7,309,336 B2 | 12/2007 | Ashley et al. | |
| 7,497,826 B2 | 3/2009 | Ouchi | |
| 7,771,422 B2 | 8/2010 | Auge et al. | |
| 2003/0229344 A1 | 12/2003 | Dycus et al. | |
| 2005/0149011 A1* | 7/2005 | Ashley | A61B 17/1671 606/41 |
| 2006/0148306 A1 | 7/2006 | Desinger et al. | |
| 2008/0009927 A1 | 1/2008 | Vilims et al. | |
| 2008/0071261 A1* | 3/2008 | Orszulak | A61B 18/14 606/34 |
| 2011/0288547 A1 | 11/2011 | Morgan et al. | |
| 2011/0299565 A1* | 12/2011 | Jester | G01R 33/285 374/161 |
| 2012/0172858 A1 | 7/2012 | Harrison et al. | |

FOREIGN PATENT DOCUMENTS

| | | |
|---|---|---|
| CN | 102341038 A | 2/2012 |
| CN | 203736302 U | 7/2014 |
| EP | 0061246 | 9/1982 |
| EP | 0750886 | 1/1997 |
| EP | 1902681 A1 | 3/2008 |
| EP | 2529687 A2 | 12/2012 |
| EP | 2620115 A1 | 7/2013 |
| GB | 2321193 | 7/1998 |
| GB | 2326519 | 12/1998 |
| WO | 9006079 A1 | 6/1990 |
| WO | WO 2006/048199 | 5/2006 |
| WO | WO 2006/081191 | 8/2006 |
| WO | 2010102117 A1 | 9/2010 |

OTHER PUBLICATIONS

Chinese Office Action and Search Report (with English translation), dated Aug. 23, 2016, corresponding to Chinese Application No. 201310717048.X; 28 total pages.

* cited by examiner

ELECTRO-THERMAL DEVICE

CROSS REFERENCE TO RELATED APPLICATION

The present application claims the benefit of and priority to U.S. Provisional Application Ser. No. 61/708,852, filed on Oct. 2, 2012, the entire contents of which are incorporated herein by reference.

BACKGROUND

Technical Field

The present disclosure relates to an electro-thermal medical device. More particularly, the present disclosure relates to an electro-thermal medical device that utilizes a double helix wound electrical configuration and an electro-thermal element configured to electrosurgically treat tissue.

Description of Related Art

Electro-thermal devices utilized in vascular energy treatment applications, such as, for example, laparoscopic ablations and/or venous reflux are well known in the medical field. Transmission of electrosurgical energy to the treatment site, namely from the electrosurgical generator to the electro-thermal device, is accomplished via an electrosurgical cable. During transmission an electrical field is generated through the electrosurgical cable. Stray electrosurgical RF energy (e.g., RF leakage) is emitted along the electrosurgical cable path, which may reduce treatment energy. Moreover, electrical fields, associated with stray RF energy, may interfere with the operation of other electronic equipment in the surgical arena, such as patient monitoring equipment.

Electro-thermal devices may include, for example, one or more devices, e.g., thermocouples, thermistors, etc., that are configured for tissue monitoring, thermal temperature control, etc. Thermocouples (and/or thermistors), however, have a slow response time and, as a result thereof, typically exhibit inadequate sensory monitoring and energy control at a treatment site with respect to RF energy and tissue parameters. Inadequate sensory monitoring and energy control at a treatment site may increase treatment dosage beyond required due to a slow response time, resulting in less than optimal clinical efficacy, which, in turn, may also create potential patient and surgeon safety concerns due to alternate site energy dosages i.e., excess RF energy leakage dosage to a patient and/or surgeon.

SUMMARY

In view of the foregoing, an electro-thermal medical device that utilizes a double helix wound electrical configuration and an electro-thermal element configured to electrosurgically treat tissue may prove advantageous in the medical arts.

Embodiments of the present disclosure are described in detail with reference to the drawing figures wherein like reference numerals identify similar or identical elements. As used herein, the term "distal" refers to the portion that is being described which is further from a user, while the term "proximal" refers to the portion that is being described which is closer to a user.

An aspect of the present disclosure provides an electro-thermal apparatus that is configured to treat tissue. The electro-thermal apparatus includes an electrosurgical cable that is configured to couple to an electrosurgical energy source. The electrosurgical cable includes supply and return lines that are wound in a double helix arrangement around a dielectric insulator within the electrosurgical cable. An electro-thermal element is provided at a distal end of the electrosurgical cable and is in electrical communication with the supply and return lines via corresponding first and second conductive traces. The first and second conductive traces have a patterned geometry and resistivity that is configured to convert electrical energy provided by the supply and return lines to thermal energy for treating tissue.

The supply and return lines may be covered by an insulative material and the first and second conductive traces may extend along an exterior surface of the end cap. The first and second conductive traces may include a patterned geometry that substantially matches the double helix arrangement of the supply and return lines around the dielectric insulator.

An end cap may be operably coupled to the electro-thermal apparatus. The end cap may include one or more sensors disposed therein that is/are positioned adjacent a distal of the electro-thermal element. The sensors may be configured to serve as a bridge to connect the first and second conductive traces. The sensor(s) may be configured to sense one or more electrical parameters such as, for example, voltage, current, impedance and power. The sensor(s) may be in operable communication with the electrosurgical energy source, e.g., through a closed-loop signal feedback control protocol, for monitoring and controlling the at least one electrical parameter. In certain instances, an aperture may extend through the dielectric insulator and may be configured to receive a lead that connects the at least one sensor to the at least one module.

An optical fiber may be provided and may include a plurality of optical gratings that are positioned adjacent the electro-thermal element and configured to sense temperature. The optical fiber may be in operable communication with the electrosurgical energy source, e.g., through a closed-loop signal feedback control protocol, for monitoring and controlling thermal energy output from the electro-thermal element. The optical fiber may be seated within a channel defined in and extending along a length of the end cap and electrosurgical cable.

An aspect of the present disclosure provides an electro-thermal apparatus that is configured to treat tissue. The electro-thermal apparatus includes an electrosurgical cable that is configured to couple to an electrosurgical energy source. The electrosurgical cable includes supply and return lines that are wound in a double helix arrangement around a dielectric insulator within the electrosurgical cable. An electro-thermal element is provided at a distal end of the electrosurgical cable and is in electrical communication with the supply and return lines via corresponding first and second conductive traces that are positioned to contact tissue. The first and second conductive traces have a patterned geometry substantially matching the double helix arrangement of the supply and return lines around the dielectric insulator. The first and second conductive traces have a resistivity that is configured to convert electrical energy provided by the supply and return lines to thermal energy for treating tissue.

An aspect of the present disclosure provides a surgical system for treating tissue. The surgical system includes an electrosurgical energy source and an electro-thermal apparatus. The electro-thermal apparatus includes an electrosurgical cable that is configured to couple to an electrosurgical energy source. The electrosurgical cable includes supply and return lines that are wound in a double helix arrangement around a dielectric insulator within the electrosurgical cable. The electro-thermal element is provided at a distal end of the electrosurgical cable and is in electrical communication with the supply and return lines via corresponding first and second conductive traces. The first and second conductive traces have a patterned geometry and resistivity that is configured to convert electrical energy provided by the supply and return lines to thermal energy for treating tissue.

The supply and return lines may be covered by an insulative material and the first and second conductive traces may extend along an exterior surface of the end cap. The first and second conductive traces may include a patterned geometry that substantially matches the double helix arrangement of the supply and return lines around the dielectric insulator.

An end cap may be operably coupled to the electro-thermal apparatus. The end cap may include one or more sensors disposed therein that is/are positioned adjacent a distal of the electro-thermal element. The sensors may be configured to serve as a bridge to connect the first and second conductive traces. The sensor(s) may be configured to sense one or more electrical parameters such as, for example, voltage, current, impedance and power. The sensor(s) may be in operable communication with the electrosurgical energy source, e.g., through a closed-loop signal feedback control protocol, for monitoring and controlling the at least one electrical parameter. In certain instances, an aperture may extend through the dielectric insulator and may be configured to receive a lead that connects the at least one sensor to the at least one module.

An optical fiber may be provided and may include a plurality of optical gratings that are positioned adjacent the electro-thermal element and configured to sense temperature. The optical fiber may be in operable communication with the electrosurgical energy source, e.g., through a closed-loop signal feedback control protocol, for monitoring and controlling thermal energy output from the electro-thermal element. The optical fiber may be seated within a channel defined in and extending along a length of the end cap and electrosurgical cable.

BRIEF DESCRIPTION OF THE DRAWING

Various embodiments of the present disclosure are described hereinbelow with references to the drawings, wherein.

DETAILED DESCRIPTION

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In accordance with the instant disclosure, an electro-thermal device that utilizes an electrosurgical cable including an internal helical configuration coupled to an electro-thermal element including external first and second conductive traces having a helical configuration is provided.

The electro-thermal device provides an integral method of converting radio frequency (RF) based electrical energy to thermal energy for purposes of treating various clinical procedures, such as, for example, vascular clinical procedures including without limitation venous reflux and laparoscopic ablations.

Figure 1:
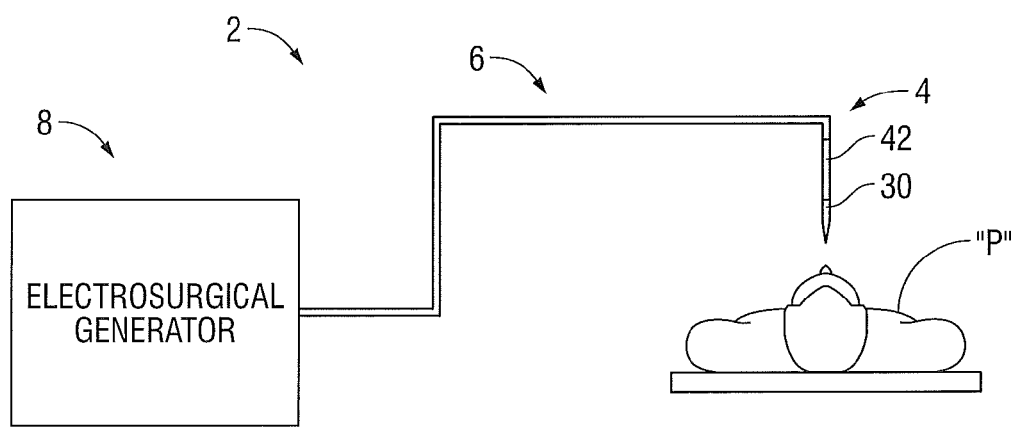
FIG. 1 is a perspective view of an electrosurgical system according to an embodiment of the instant disclosure.

FIG. 1 shows an electrosurgical system 2 (system 2) according to the present disclosure. The system 2 is an electrosurgical system that includes an electro-thermal device 4 (device 4) that couples via an electrosurgical cable 6 (cable 6) to an electrosurgical energy source, e.g., an electrosurgical generator 8 (generator 8). Device 4 includes an electro-thermal element 31 for treating tissue of a patient P (FIG. 3) and an end cap 30 including one or more sensors 38 for monitoring tissue treatment energy applied to tissue of a patient P (FIG. 3), as described in greater detail below. Electrosurgical RF energy is supplied to the device 4 by generator 8 via a supply line 10 (FIG. 3) and energy is returned to generator 8 through a return line 12 (FIG. 3).

Figure 2:
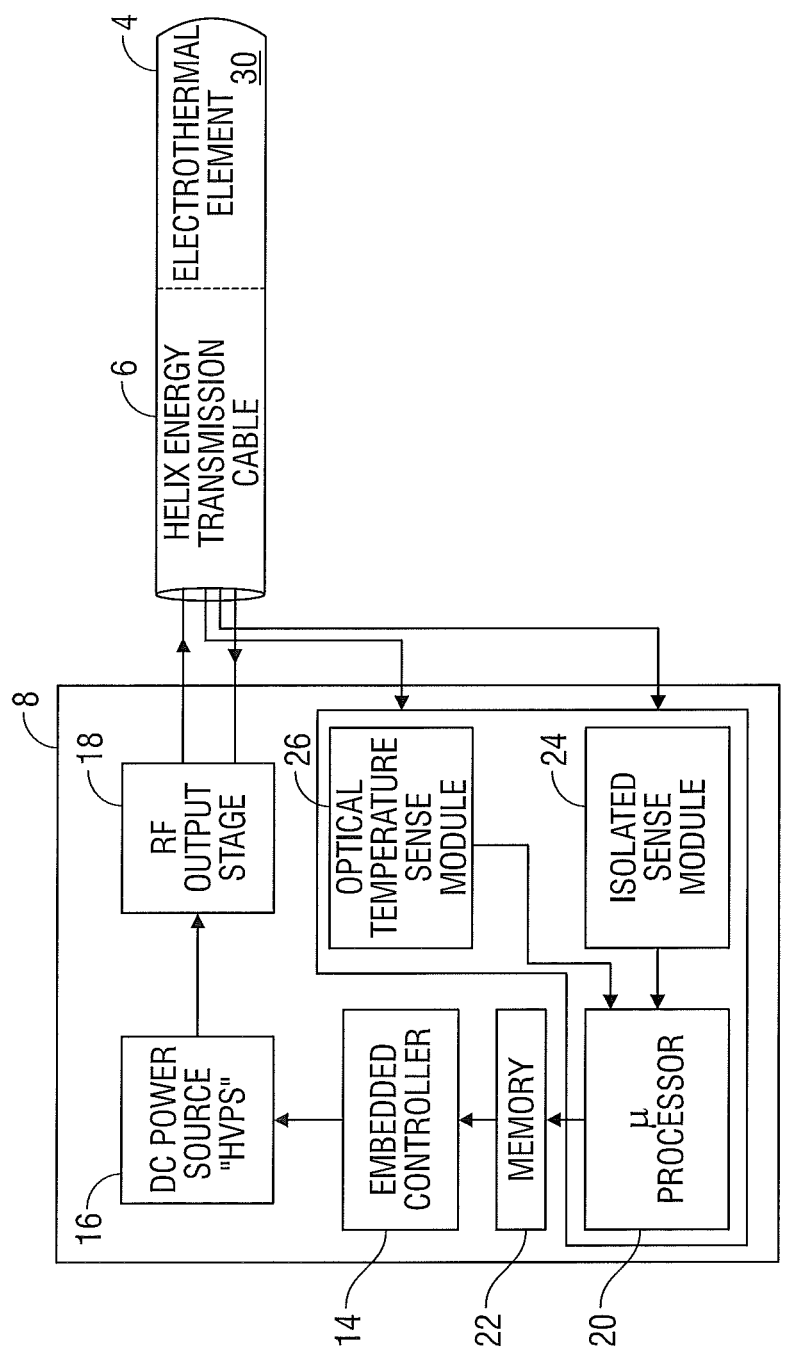
FIG. 2 is a schematic block diagram of the electrosurgical system depicted in FIG. 1.

FIG. 2 shows a schematic block diagram of generator 8. Briefly, generator 8 includes a controller 14, a high voltage power supply 16 ("HVPS 16") and an RF output stage 18. HVPS 16 provides DC power to the RF output stage 18, which, in turn, converts DC power into RF energy and delivers the RF energy to device 4. Controller 14 includes one or more microprocessors 20 operatively connected to a memory 22 which may be volatile type memory (e.g., RAM) and/or non-volatile type memory (e.g., flash media, disk media, etc.). In the illustrated embodiment, microprocessor 20 communicates with an isolated sense module 24 and an optical temperature sense module 26 (FIG. 2). Module 24 is configured for a closed-loop signal feedback control protocol for monitoring and controlling one or more electrical parameters, such as, for example, voltage, current, impedance and power. Likewise, module 26 is configured for a closed-loop signal protocol, e.g., temperature feedback control, via optical sensor processing for monitoring and controlling thermal energy output from electro-thermal element 31 of device 4, as described in greater detail below. In an embodiment, isolated sense module 24 provides a conversion of sensed RF energy parameters, e.g., impedance, communicated from a tissue site through an isolation barrier and introduces patient safety between the generated RF energy and ground. Specifically, the isolation barrier provides high impedance insulative quality that isolates the monitored energy signal(s) of sensor 38 from the electrosurgical generator to prevent leakage energy shock hazard to the patient and/or surgeon. The isolation barrier may incorporate without limitation, a magnetic coupling, air core or optical coupling device or other suitable device(s).

Figure 3:
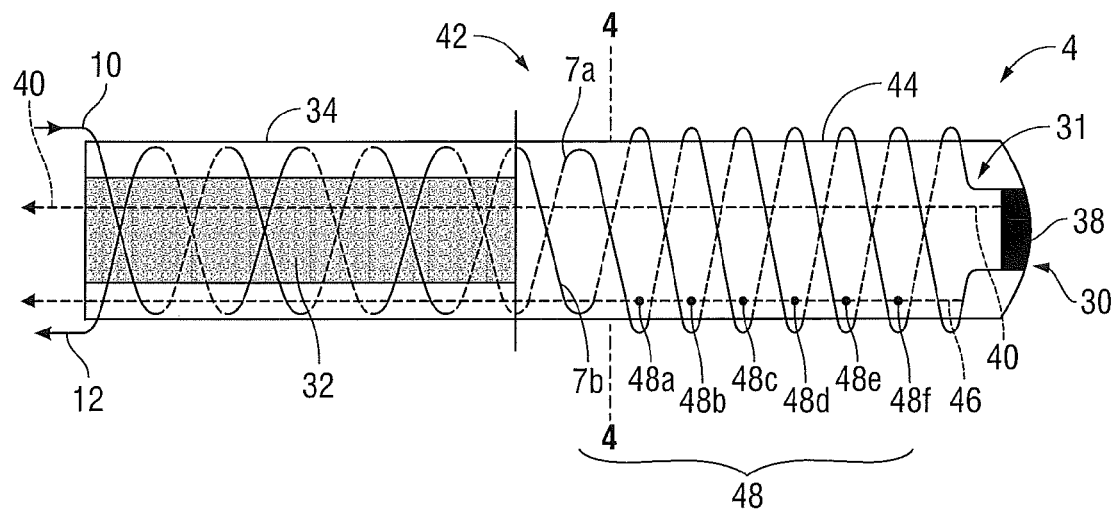
FIG. 3 is a side view of a portion of an electrosurgical cable depicted in FIGS. 1 and 2.

FIG. 3 shows a cross-sectional view of cable 6. Cable 6 includes a plurality of electrical conductors in the form of supply and return lines 10, 12. Supply and return lines 10, 12 may be configured with wire, copper traces, or ink deposition conductors which are insulated via one or more suitable types of insulating materials, e.g., a removable plastic sheathing (not explicitly shown). In accordance with the instant disclosure, supply and return lines 10, 12 are wound in a helix configuration and may be of any length depending on the geometric and physical properties (e.g., tensile strength, flexibility, etc.) of materials used in manufacturing of cable components. Supply and return lines 10, 12 are oriented in a double helix arrangement that includes two congruent helixes with the same axis, differing by a translation along the axis. The arrangement of the supply and return lines 10, 12 in a double helix configuration orients the opposing electrical fields generated by the electrosurgical RF energy passing therethrough to mitigate and/or cancel out thereby minimizing the amount of stray electrical RF energy. More specifically, placement and orientation of supply and return lines 10, 12 in a double helix configuration provides for close proximity of electrical fields generated during transmission of electrosurgical RF energy and maximizes amount of energy delivered to the treatment site. Other positive attributes associated with placement and orientation of supply and return lines 10, 12 in the double helix configuration may include, but are not limited to: increased safety of personnel and the patient; decreased capacitive and RF field leakage, which, in turn, may improve RF control of the delivered energy; decreased RF transmission loss, which, in turn, may improve efficiency of the generator 36; and decreased RF noise to additional equipment found in (or adjacent) the surgical room, such as patient monitoring equipment.

Continuing with reference to FIG. 3, supply and return lines 10, 12 are wound within cable 6 around a dielectric insulator 32 (insulator 32), which provides support for the supply and return lines 10, 12 and an insulative sheath 34 that covers supply and return lines 10, 12. Insulator 32 and the sheath 34 may be formed from the same type of material.

Figure 4:
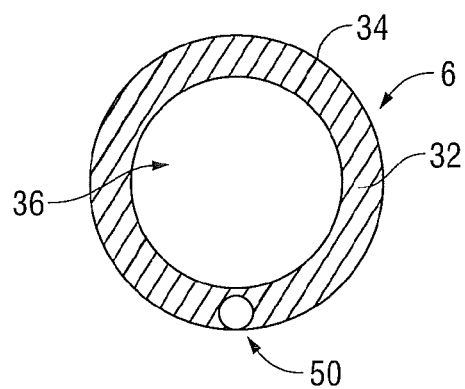
FIG. 4 is a cross-sectional view taken along line-segment "4-4" in FIG. 3.

An aperture 36 (FIG. 4) of suitable configuration extends through insulator 32 and is configured to receive a lead 40 (FIG. 3) therein for connecting one or more sensors 38 to isolated sense module 24. As can be appreciated, extending lead 40 through aperture 36 reduces (if not eliminates) the occurrence of residual stray electrical RF energy interfering with feedback signals transmitted along lead 40, i.e., lead 40.

Referring again to FIGS. 1 and 3, device 4 is illustrated including a generally elongated configuration to facilitate insertion into a body of a patient, e.g., through a cannula, natural body orifice, etc. Device 4 may include other configurations to accommodate various surgical procedures. Device 4 may be formed from any suitable material, including but not limited to metal, plastic, ceramic material, etc. In the illustrated embodiment, device 4 is made from a relatively pliable plastic that is configured to facilitate positioning device 4 adjacent tissue of interest.

Device 4 includes a proximal end 42 (not shown to scale in FIG. 3) that operably couples via suitable coupling methods to a distal end (not explicitly shown) of cable 6. As defined herein, the distal end of cable 6 refers to that portion of cable 6 that is positioned within device 4. In the illustrated embodiment, proximal end 42 is positioned over at least a portion of the distal end of cable 6 and is held into place via mechanical or adhesive methods, friction or press fit, etc. Proximal end 42 is positioned over the distal end of cable 6 such that supply and return lines 10, 12 may be coupled, e.g., via a bead of solder, or alternately coupled to first and second conductive traces 7a, 7b, via a conductive continuum using laser etched copper traces or ink deposition, respectively (FIG. 3) of electro-thermal element 31. Moreover, conductive traces 7a, 7b are electrically coupled to sensor(s) 38 of end cap 30 by one or more suitable coupling methods including, but not limited to a mechanical spring contact, friction or press fit, adhesive or solder.

In embodiments, proximal end 42 is configured to serve as a handle to facilitate intravascular navigation of device 4. In this instance, electro-thermal element 31 including conductive traces 7a, 7b extend a predetermined distance from proximal 42 so as to provide an adequate area for a user to grasp proximal end 42 and to provide an adequate treatment area for treating tissue of a patient. In the instance where proximal end 42 serves as a handle, proximal end 42 may be formed from or coated with a non-conductive material.

With continued reference to FIG. 3, electro-thermal element 31 is operable to electrosurgically treat tissue. To this end, electro-thermal element 31 is in electrical communication with supply and return lines 10, 12 via corresponding first and second conductive traces 7a, 7b that are coupled to one another via sensor(s) 38 of end cap 30.

Conductive traces 7a, 7b have a patterned geometry and resistivity that is configured to convert electrical energy provided by supply and return lines 10, 12 to thermal energy for treating tissue. In the illustrated embodiment, conductive traces 7a, 7b include a patterned geometry that substantially matches the double helix wound configuration of the supply and return lines, as best seen in FIG. 3. The specific configuration, e.g., spacing between the two congruent helixes that form conductive traces 7a, 7b, may be altered to accommodate specific configurations of device 4, specific surgical procedures, manufacturers' preference, etc. For example, in the illustrated embodiment, conductive traces 7a, 7b are illustrated having a double helix configuration that is "tighter" than the double helix configuration of supply and return lines 10, 12. This tightness provides a specific resistivity and electro-thermal output to effectively treat tissue.

Continuing with reference to FIG. 3, end cap 30 operably couples, via one or more suitable coupling methods (e.g., adhesive), to a distal end of electro-thermal element 31 of device 4. In the illustrated embodiment, sensor 38 is shown positioned within end cap 30 adjacent a distal end of electro-thermal element 31 and couples conductive traces 7a, 7b to one another. Specifically, sensor 38 serves as a bridge to connect conductive traces 7a, 7b to one another and is configured to sense one or more electrical parameters, e.g., voltage, current, impedance and power, as electro-thermal energy is being conducted from conductive traces 7a, 7b. Sensor 38 provides information pertaining to one or more of the aforementioned electrical parameters to module 24 in the closed-loop feedback protocol described above. With this purpose in mind, sensor 38 will have a nominal resistance. In embodiments, sensor 38 includes a resistance that may range from about 0.01 ohms to about 10.0 ohms. In some embodiments, sensor 38 may include resistance values that are less than 0.01 ohms and greater than about 10.0 ohms.

With continued references to FIG. 3, an optical fiber 46 is illustrated including a plurality of optical gratings 48 that are positioned adjacent electro-thermal element. In the illustrated embodiment, at least but not limited to six (6) optical gratings 48a-48f are configured to sense temperature as electro-thermal energy is being conducted from conductive traces 7a, 7b. Optical gratings 48a-48f provide information pertaining to tissue temperature (or conductive traces 7a, 7b) to module 26 in the closed-loop feedback protocol described above. Optical fiber 46 is seated within a channel 50 (FIG. 4) that is defined in and extends along a length of device 4 and cable 6. Sheath 34 or other suitable material may be utilized to cover the channel 50. For illustrative purposes, sheath 34 is shown covering channel 50.

In one particular embodiment of the present disclosure, device 4 may be inserted through an orifice (e.g., cannula) in a patient's body and navigated to a position adjacent tissue of interest. Generator 8 is activated and RF energy is transmitted via supply and return lines, 10, 12 to electro-thermal element 31 of device 4. The RF energy is provided to conductive traces 7a, 7b and converted to elector-thermal energy via the resistivity of conductive traces 7a, 7b and specific patterned geometry thereof to electro-thermally treat tissue of interest.

As tissue is being electro-thermally being treated, sensor 38 and optical gratings 48a-48f provide relevant information to respective modules 24, 26. This relevant information is processed by microprocessor 20 and utilized by controller 14 to control RF output of generator 8.

The unique configuration of device 4 including the electro-thermal element 31, and end cap 30 allows a user to electro-thermally treat tissue while maintaining the double helix configuration of cable 6 thus, mitigating the likelihood of stray electrosurgical RF energy at device 4. Moreover, sensor 38 and optical grating 48a-48f provide a fast response time and exhibit adequate sensory monitoring and energy control at a treatment site with respect to RF energy and tissue parameters, which, in turn, may reduce potential patient and surgeon safety concerns due to excess RF energy leakage dosage to a patient and/or surgeon.

From the foregoing and with reference to the various figure drawings, those skilled in the art will appreciate that certain modifications can also be made to the present disclosure without departing from the scope of the same. For example, one or more control buttons (not explicitly shown) may be provided on device 4 and utilized to control one or more parameters of generator 8, e.g., on/off button to control activation and de-activation of generator 8.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electro-thermal apparatus configured to treat tissue, comprising:
   an electrosurgical cable having a proximal portion configured to couple to an electrosurgical energy source and a distal portion including a supply line and a return line, the supply and return lines together forming a double helix configuration having a first pitch; and
   an electro-thermal element having a first conductive trace in electrical communication with the supply line and a second conductive trace in electrical communication with the return line, the first and second conductive traces together forming a double helix configuration having a second pitch different than the first pitch of the double helix configuration of the supply and return lines to provide a thermal resistivity and electro-thermal output that are configured to convert electrical energy provided by the supply and return lines to thermal energy for treating tissue.

2. The electro-thermal apparatus according to claim 1, wherein the supply and return lines are covered by an insulative material.

3. The electro-thermal apparatus according to claim 1, further comprising an end cap operably coupled to a distal portion of the electro-thermal element, the end cap including at least one sensor connected to a distal portion of each of the first and second conductive traces.

4. The electro-thermal apparatus according to claim 3, wherein the at least one sensor is configured to sense at least one electrical parameter selected from the group consisting of voltage, current, impedance and power.

5. The electro-thermal apparatus according to claim 3, wherein the at least one sensor is in operable communication with the electrosurgical energy source through a closed-loop signal feedback control protocol.

6. The electro-thermal apparatus according to claim 5, further comprising:
   a dielectric insulator extending longitudinally through a channel cooperatively defined by the supply and return lines; and
   a lead extending longitudinally through the dielectric insulator and connecting the at least one sensor to the electrosurgical energy source.

7. The electro-thermal apparatus according to claim 1, further including an optical fiber including a plurality of optical gratings positioned adjacent the electro-thermal element and configured to sense temperature.

8. The electro-thermal apparatus according to claim 7, wherein the optical fiber is in operable communication with the electrosurgical energy source through a closed-loop signal feedback control protocol, the closed-loop signal feedback control protocol configured to control thermal energy output from the electro-thermal element.

9. The electro-thermal apparatus according to claim 8, wherein the optical fiber is disposed within a channel defined in and extending along a length of the electro-thermal element and the electrosurgical cable.

10. The electro-thermal apparatus according to claim 1, wherein the resistivity of the first and second conductive traces is different than a resistivity of the supply and return lines.

11. The electro-thermal apparatus according to claim 1, wherein the first pitch of the supply and return lines is larger than the second pitch of the first and second conductive traces.

12. A surgical system for treating tissue, comprising:
   an electrosurgical energy source; and
   an electro-thermal apparatus including:
      an electrosurgical cable having a proximal portion configured to couple to the electrosurgical energy source and a distal portion including a supply line and a return line, the supply and return lines together forming a double helix configuration having a first pitch; and
      an electro-thermal element having a first conductive trace in electrical communication with the supply line and a second conductive trace in electrical communication with the return line, the first and second conductive traces together forming a double helix configuration having a second pitch different than the first pitch of the double helix configuration of the supply and return lines to provide a thermal resistivity and electro-thermal output that are configured to convert electrical energy provided by the supply and return lines to thermal energy for treating tissue.

13. The surgical system according to claim 12, wherein the supply and return lines are covered by an insulative material.

14. The surgical system according to claim 12, further comprising an end cap operably coupled to a distal portion of the electro-thermal element, the end cap including at least one sensor connected to a distal portion of each of the first and second conductive traces.

15. The surgical system according to claim 14, wherein the at least one sensor is configured to sense at least one electrical parameter selected from the group consisting of voltage, current, impedance and power.

16. The surgical system according to claim 14, wherein the at least one sensor is in operable communication with the electrosurgical energy source through a closed-loop signal feedback control protocol.

17. The surgical system according to claim 16, further comprising:
- a dielectric insulator extending longitudinally through a channel cooperatively defined by the supply and return lines; and
- a lead extending longitudinally through the dielectric insulator and connecting the at least one sensor to the at electrosurgical energy source.

18. The surgical system according to claim 12, further including an optical fiber including a plurality of optical gratings positioned adjacent the electro-thermal element and configured to sense temperature.

19. The surgical system according to claim 18, wherein the optical fiber is in operable communication with the electrosurgical energy source through a closed-loop signal feedback control protocol, the closed-loop signal feedback control protocol configured to control thermal energy output from the electro-thermal element, wherein the optical fiber is disposed within a channel defined in and extending along a length of the electro-thermal element and the electrosurgical cable.

20. The surgical system according to claim 12, wherein the resistivity of the first and second conductive traces is different than a resistivity of the supply and return lines.

* * * * *